United States Patent
Schachar (12)
(10) Patent No.: US 6,197,056 B1
(45) Date of Patent: Mar. 6, 2001

(54) SEGMENTED SCLERAL BAND FOR TREATMENT OF PRESBYOPIA AND OTHER EYE DISORDERS

(75) Inventor: Ronald A. Schachar, Dallas, TX (US)

(73) Assignee: RAS Holding Corp., Dallas, TX (US)

(*) Notice: Subject to any disclaimer, the term of this patent is extended or adjusted under 35 U.S.C. 154(b) by 0 days.

(21) Appl. No.: 09/032,830

(22) Filed: Mar. 2, 1998

Related U.S. Application Data (60) Continuation-in-part of application No. 08/462,649, filed on Jun. 5, 1995, now Pat. No. 5,722,952, which is a division of application No. 08/139,756, filed on Oct. 22, 1993, now Pat. No. 5,489,299, which is a division of application No. 07/913,486, filed on Jul. 15, 1992, now Pat. No. 5,354,331.

(51) Int. Cl.[7] .................................................. A61F 2/14
(52) U.S. Cl. ................................................................ 623/4.1
(58) Field of Search .......................... 623/4, 6, 4.1, 5.12, 623/6.11; 424/427

(56) References Cited

U.S. PATENT DOCUMENTS

| Re. 35,974 | * 12/1998 | Davenport ................................. 623/4 |
|---|---|---|
| 2,952,023 | 9/1960 | Rosen . |
| 3,064,643 | 11/1962 | Dixon . |
| 3,454,966 | 7/1969 | Rosen . |
| 3,884,236 | 5/1975 | Krasnov . |
| 4,174,389 | 11/1979 | Cope . |
| 4,549,529 | 10/1985 | White . |
| 4,603,697 | 8/1986 | Kamerling . |
| 4,782,820 | 11/1988 | Woods . |
| 4,839,342 | 6/1989 | Kaswan . |
| 4,923,699 | 5/1990 | Kaufman . |
| 4,966,452 | 10/1990 | Shields et al. . |
| 4,976,719 | 12/1990 | Siepser . |
| 5,025,811 | 6/1991 | Dobrogowski et al. . |
| 5,152,759 | 10/1992 | Parel et al. . |
| 5,152,760 | 10/1992 | Latina . |
| 5,163,419 | 11/1992 | Goldman . |
| 5,174,304 | 12/1992 | Latina et al. . |
| 5,181,922 | 1/1993 | Blumenkanz et al. . |
| 5,267,553 | * 12/1993 | Graether .................................... 623/4 |
| 5,292,514 | * 3/1994 | Capecchi .................................... 623/4 |
| 5,300,114 | * 4/1994 | Gwon ........................................ 623/4 |
| 5,300,144 | 4/1994 | Adams ................................... 106/162 |
| 5,312,394 | 5/1994 | Beckman . |
| 5,354,331 | 10/1994 | Schachar . |
| 5,372,595 | 12/1994 | Gaasterland et al. . |
| 5,472,436 | * 12/1995 | Fremstad .................................. 623/4 |
| 5,476,511 | * 12/1995 | Gwon ........................................ 623/4 |

FOREIGN PATENT DOCUMENTS

| 1597188 | 10/1990 | (SU) . |
|---|---|---|
| 1639647 | 4/1991 | (SU) . |
| WO 89/09034 | 10/1989 | (WO) . |

\* cited by examiner

*Primary Examiner*—Michael J. Milano (57) ABSTRACT

A segmented scleral expansion band adapted for implantation within or fastening to a segment of the sclera of an eye lying outside of and adjacent to the ciliary body of the eye, is formed from a number of arcuate segments, curved to match the curvature of the globe of the eye, and joined together at each end to form a complete scleral expansion band. The band is implanted in the sclera of the eye by forming circumferential tunnels, inserting the band segments through the tunnels, and joining the ends of the segments to form a complete scleral expansion band. The scleral expansion band is useful in treating presbyopia and other ocular disorders.

30 Claims, 5 Drawing Sheets

SEGMENTED SCLERAL BAND FOR TREATMENT OF PRESBYOPIA AND OTHER EYE DISORDERS

RELATIONSHIP TO OTHER APPLICATIONS

This application is a continuation-in-part of copending application Ser. No. 08/462,649, filed Jun. 5, 1995 U.S. Pat. No. 5,722,952, which is a divisional of U.S. application Ser. No. 08/139,756, filed, Oct. 22, 1993, now U.S. Pat. No. 5,489,299, which is a divisional of U.S. application Ser. No. 07/913,486, filed Jul. 15, 1992, now U.S. Pat. No. 5,354,331.

BACKGROUND OF THE INVENTION

1. Field of the Invention

This invention relates to methods of treating presbyopia, hyperopia, primary open angle glaucoma and ocular hypertension and more particularly to methods of treating these diseases by increasing the effective working distance of the ciliary muscle. The invention also relates to increasing the amplitude of accommodation of the eye by increasing the effective working range of the ciliary muscle and to prosthetic devices for achieving such increased amplitude of accommodation.

2. Brief Description of the Prior Art

In order for the human eye to have clear vision of objects at different distances, the effective focal length of the eye must be adjusted to keep the image of the object focused as sharply as possible on the retina. This change in effective focal length is known as accommodation and is accomplished in the eye by varying the shape of the crystalline lens. Generally, in the unaccommodated emmetropic eye the curvature of the lens is such that distant objects are sharply imaged on the retina. In the unaccommodated eye, near objects are not focused sharply on the retina because their images lie behind the retinal surface. In order to visualize a near object clearly, the curvature of the crystalline lens is increased, thereby increasing its refractive power and causing the image of the near object to fall on the retina.

The change in shape of the crystalline lens is accomplished by the action of certain muscles and structures within the eyeball or globe of the eye. The lens is located in the forward part of the eye, immediately behind the pupil. It has the shape of a classical biconvex optical lens, i.e., it has a generally circular cross section having two convex refracting surfaces, and is located generally on the optical axis of the eye, i.e., a straight line drawn from the center of the cornea to the macula in the retina at the posterior portion of the globe. In the unaccommodated human eye the curvature of the posterior surface of the lens, i.e., the surface adjacent to the vitreous body, is somewhat greater than that of the anterior surface. The lens is closely surrounded by a membranous capsule that serves as an intermediate structure in the support and actuation of the lens. The lens and its capsule are suspended on the optical axis behind the pupil by a circular assembly of very many radially directed elastic fibers, the zonules, which are attached at their inner ends to the lens capsule and at their outer ends to the ciliary body, a muscular ring of tissue, located just within the outer supporting structure of the eye, the sclera. The ciliary muscle is relaxed in the unaccommodated eye and therefore assumes its largest diameter.

According to the classical theory of accommodation, originating with Helmholtz, the relatively large diameter of the ciliary muscle in this condition causes a tension on the zonules which in turn pulls radially outward on the lens capsule, causing the equatorial diameter of the lens to increase slightly and decreasing the anterior-posterior dimension of the lens at the optical axis. Thus, the tension on the lens capsule causes the lens to assume a flattened state wherein the curvature of the anterior surface, and to some extent the posterior surface, is less than it would be in the absence of the tension. In this state the refractive power of the lens is relatively low and the eye is focused for clear vision of distant objects.

When the eye is intended to be focused on a near object, the ciliary muscles contract. According to the classical theory, this contraction causes the ciliary muscle to move forward and inward, thereby relaxing the outward pull of the zonules on the equator of the lens capsule. This reduced zonular tension allows the elastic capsule of the lens to contract, causing an increase in the antero-posterior diameter of the lens (i.e., the lens becomes more spherical) resulting in an increase in the optical power of the lens. Because of topographical differences in the thickness of the lens capsule, the central anterior radius of curvature decreases more than the central posterior radius of curvature. This is the accommodated condition of the eye wherein the image of near objects falls sharply on the retina.

Presbyopia is the universal decrease in the amplitude of accommodation that is typically observed in individuals over 40 years of age. In the person having normal vision, i.e., having emmetropic eyes, the ability to focus on near objects is gradually lost, and the individual comes to need glasses for tasks requiring near vision, such as reading.

According to the conventional view the amplitude of accommodation of the aging eye is decreased because of the loss of elasticity of the lens capsule and/or sclerosis of the lens with age. Consequently, even though the radial tension on the zonules is relaxed by contraction of the ciliary muscles, the lens does not assume a greater curvature. According to the conventional view, it is not possible by any treatment to restore the accommodative power to the presbyopic eye. The loss of elasticity of the lens and capsule is seen as irreversible, and the only solution to the problems presented by presbyopia is to use corrective lenses for close work, or bifocal lenses, if corrective lenses are also required for distant vision.

Certain rings and/or segments have been used in ocular surgery for various purposes. Rings and/or segments of flexible and/or elastic material, attached or prepared in situ by fastening the ends of strips of the material around the posterior portion of the globe, posterior to the pars plana (over the underlying retina), have been used to compress the sclera in certain posterior regions. Supporting rings of metal, adapted to fit the contour of the sclera have been used as temporary supporting structures during surgery on the globe. However, none of these known devices has been used for surgical treatment of presbyopia, and none has been adapted to the special needs of prosthetic devices used in treating presbyopia.

A scleral band adapted to be fastened to the sclera of the eye in the region of the ciliary body in order to expand the sclera in that region and thereby increase the working distance of the ciliary muscle is described in applicant's U.S. Pat. No. 5,354,331, the entire disclosure of which is incorporated herein by reference. The scleral band of that patent is manufactured as a single unitary device that is placed on the surface of the sclera and fastened thereto, e.g., by suturing. Although the band is effective, alternative designs are possible that permit greater flexibility in installing the scleral band.

Accordingly, a need has continued to exist for a scleral band for treating presbyopia and other eye disorders that allows the surgeon the opportunity of other methods of installing or implanting the band.

SUMMARY OF THE INVENTION

An alternative design for a scleral band that can be implanted to treat presbyopia and other eye disorders is found in the band of this invention wherein a scleral band comprises a plurality of segments that can be assembled on the eye to form a complete scleral band. The invention also comprises a method for installing such a segmented band comprising the steps of forming tunnels in the substance of the sclera in the region overlying the ciliary body, inserting segments of the segmented band into the tunnels, and uniting the ends of the segments to form a unitary scleral band.

Accordingly, it is an object of the invention to provide a treatment for presbyopia.

A further object is to provide a treatment for presbyopia by increasing the effective working distance of the ciliary muscle in the presbyopic eye.

A further object is to provide a treatment for presbyopia by increasing the radial distance between the equator of the crystalline lens and the ciliary body.

A further object is to provide a treatment for presbyopia by implanting in the sclera in the region overlying the ciliary body a generally rigid band whereby the sclera is expanded in the region of the ciliary body.

A further object is to provide a segmented scleral band that can be assembled on the eye to provide a generally rigid band.

A further object is to provide a segmented scleral band having segments that can be inserted into tunnels prepared in the substance of the sclera and assembled thereafter to provide a generally rigid band.

A further object is to provide a treatment for hyperopia.

A further object is to provide a treatment for primary open angle glaucoma.

A further object is to provide a treatment for ocular hypertension.

A further object is to provide a treatment for increasing the amplitude of accommodation of the eye.

Further objects of the invention will become apparent from the description of the invention which follows.

DETAILED DESCRIPTION OF THE INVENTION AND PREFERRED EMBODIMENTS

This invention is based on a theory of presbyopia different from the classical theory of Helmholtz. Although the scope of the invention is not to be bound or limited by the inventor's theory, it is the inventor's view that the presbyopic loss of accommodation is due to decreased working distance of the ciliary muscle. This theory is described in more detail in U.S. Pat. No. 5,354,331, referenced above and incorporated herein by reference. Consequently, according to the invention, presbyopia is treated by increasing the effective working distance of the ciliary muscle. This is accomplished by increasing the distance between the ciliary muscle and the lens equator by increasing the diameter of the sclera in the region of the ciliary body.

According to the invention, the effective working distance of the ciliary muscle is increased by implanting in tunnels or pockets surgically formed within the tissue of the sclera of the eye a plurality of scleral band segments. The segments are then joined to form a complete scleral expansion band implanted at least partially within the sclera of the eye. The completed scleral expansion band is sized to be slightly larger than the sclera in the region of the ciliary body. Accordingly, the scleral expansion band exerts an outward traction on the sclera, thereby expanding it slightly generally in the plane of the crystalline lens. The scleral expansion also expands, i.e., increases the diameter, of the ciliary body which lies immediately inside or beneath the sclera and is anatomically attached thereto.

Figure 1:
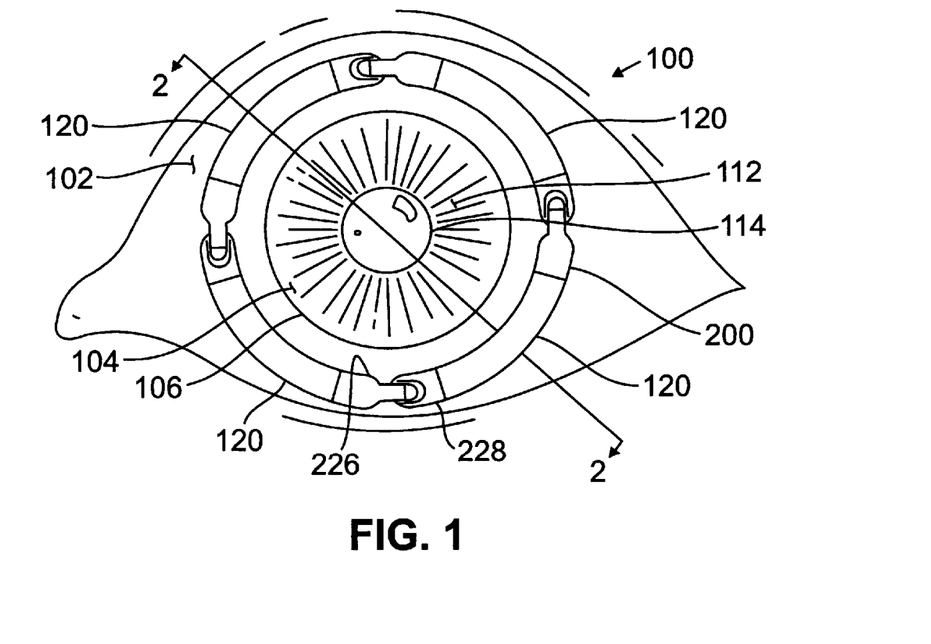
FIG. 1 illustrates a front elevational view of human eye with a scleral expansion band of the invention implanted therein.
Figure 2:
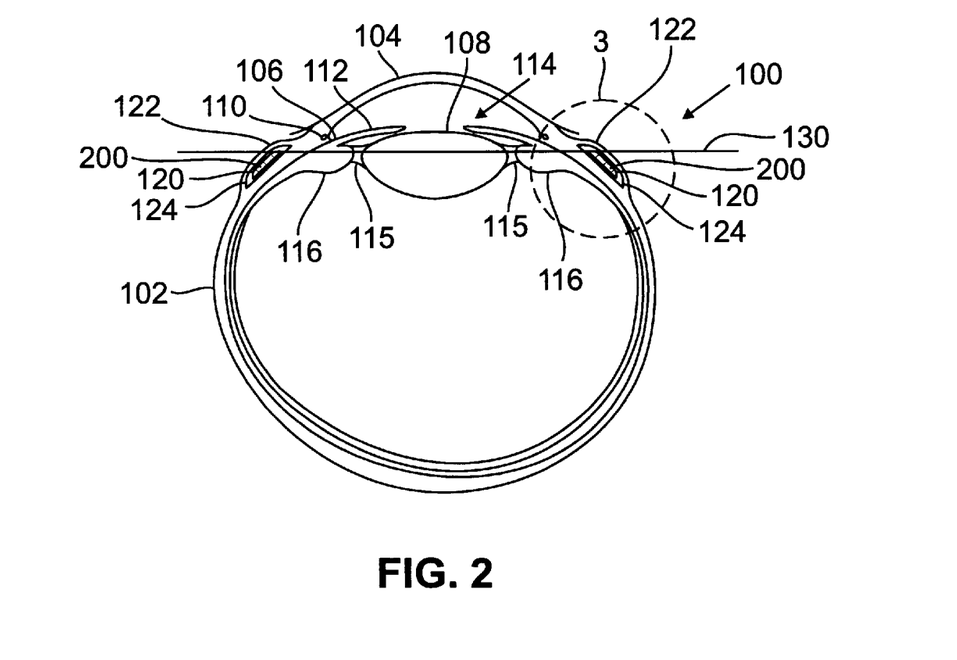
FIG. 2 shows a cross-section of the eye shown in FIG. 1 along the line 2—2.
Figure 3:
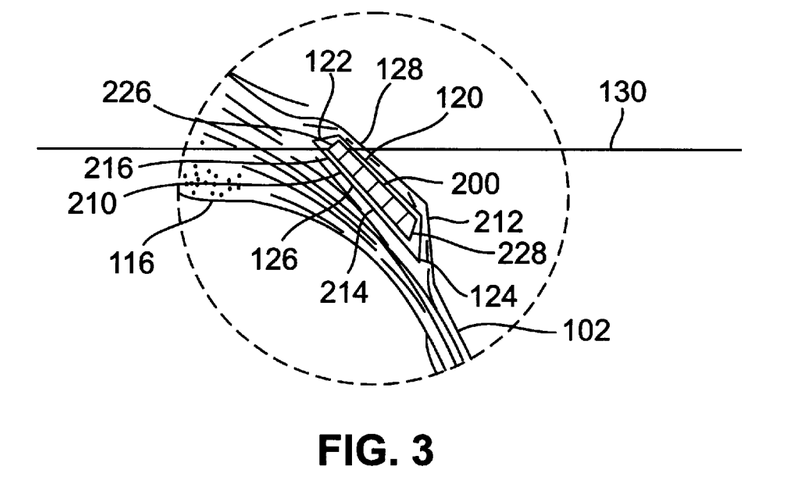
FIG. 3 shows an enlarged view of the cross section of FIG. 4 in the region indicated by the circle 3.

The relevant anatomy of the eye for understanding the operation of the scleral expansion band of the invention and for locating the scleral pockets may be seen by reference to FIGS. 1–3. FIG. 1 shows an eye 100 provided with a scleral expansion band according to the invention. The outermost layer of the eye 100 comprises the white, tough sclera 102 which encompasses most of the globe and the transparent cornea 104, which constitutes the anterior segment of the outer coat. The circular junction of the cornea and sclera is the limbus 106. Within the globe of the eye, as illustrated in the cross-section of FIG. 2, taken along line 2—2 in FIG. 1, the crystalline lens 108 is enclosed in a thin membranous capsule and is located immediately posterior to the iris 112, suspended centrally posterior to the pupil 114 on the optical axis of the eye. The lens 108 is suspended by zonules 115 extending between the lens capsule at the equator 110 of the lens 108 and the ciliary body 116. The ciliary body 116 lies just under the sclera 102 (i.e., just inwardly of the sclera 102) and is attached to the inner surface of the sclera 102. As may be seen in FIG. 2, the ciliary body 116 lies generally in a plane 130 defined by the equator 110 of the lens 108. The plane 130 can also be extended to intersect the sclera 102 whereby it forms a generally circular intersection located about 2 millimeters posterior to the limbus 106.

According to the invention a generally outwardly directed traction is exerted on the sclera in the region of the ciliary body to expand the sclera 102 in that region. This expansion of the sclera 102 produces a corresponding expansion of the attached ciliary body 116 and moves the ciliary body 116 outwardly away from the equator of the lens 108, generally in the plane 130 of the equator 110 of the lens 108. The sclera 102 is preferably expanded approximately in the plane of the equator of the lens 108. However, any expansion of the sclera 102 in the region of the ciliary body 116, i.e., in the region or zone of the sclera extending somewhat anterior or posterior to the plane of the equator 110 of the lens 108 is within the scope of the invention, provided that such expansion of the sclera 102 moves the ciliary body 116 away from the equator 110 of the lens 108. Typically, the expansion of the sclera will be accomplished in the region or zone from about 1.5 millimeters anterior to the plane 130 of the equator of the lens 108 to about 2.5 millimeters posterior to that plane, i.e., from about 0.5 millimeters to about 4.5 millimeters posterior to the limbus 106. Accordingly, the scleral pocket or tunnel 120 will be located in that region or zone of the sclera.

The scleral band 200 of the invention is assembled from a plurality of segments 202. The assembled band 200, as seen in FIGS. 1, 4, 5 and 6, has an anterior rim 226, a posterior rim 228 and a web structure 230 connecting the two rims. In order to apply the desired outward traction on the sclera at the region of the ciliary body, at least a circumferential portion of the band, i.e., either the anterior rim 226, the posterior rim 228, or the connecting web structure 230, is designed to have a diameter, when the band is assembled, slightly greater than the diameter of the sclera at the location where the band is implanted. Of course, the entire band may have a size slightly greater than the sclera. The outward tension on the sclera is applied in the region of the ciliary body as illustrated in FIGS. 2, which shows a cross-section of the eye with the scleral band 200 of the invention implanted, and in FIG. 3, which shows a detail of the cross-section of the eye as indicated by the dashed circle 3 in FIG. 2. The scleral expansion band 200 is shown within the scleral tunnel 120, which has a base 126, an outer flap 128, an anterior margin 122 and a posterior margin 124. The scleral band 200 within the tunnel or pocket 120 exerts an outward force on the outer flap 128 of the scleral pocket 120 because the band is generally larger in diameter than the sclera at the zone where the band is implanted. The outer flap 128 then transfers the outward traction via its connection to the rest of the sclera at the anterior margin 122 and posterior margin 124. Thereby, the sclera is expanded in a zone surrounding the ciliary body 116 and causes the attached ciliary body 116 to be increased in diameter as well. Accordingly, the scleral pockets or tunnels 120, which resemble belt loops through which the scleral expansion band is threaded, are located in the region of the ciliary body, and generally close to a plane defined by the equator of the crystalline lens. Thus, the scleral expansion band is positioned with respect to the antero-posterior axis of the globe of the eye, such that it will exert a traction on the sclera that will produce a radial expansion of the ciliary body located just beneath or within the sclera.

The scleral band and its segments are illustrated in FIGS. 4–11 of the drawings wherein the reference numerals refer to the same parts throughout. The scleral band 200 is comprised of a plurality of segments 202. The band 200 is designed to be applied to the sclera of the eye by forming scleral pockets or tunnels in the sclera, then passing a segment 202 through each of the tunnels and fastening the ends of the segments together to form a complete band.

Figure 4:
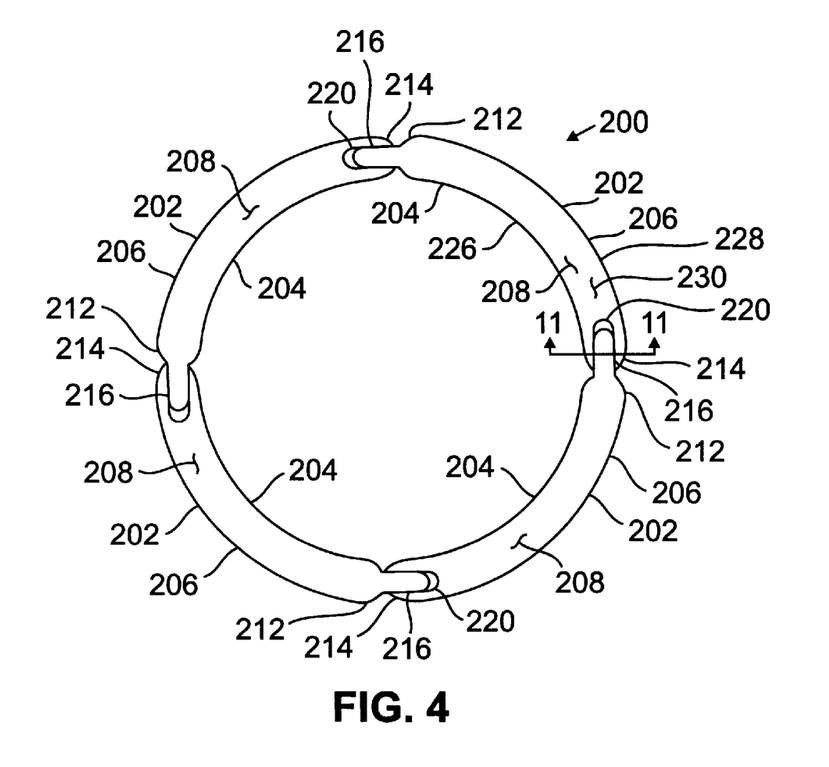
FIG. 4 shows a front elevational view of the segmented scleral band of the invention.
Figure 5:
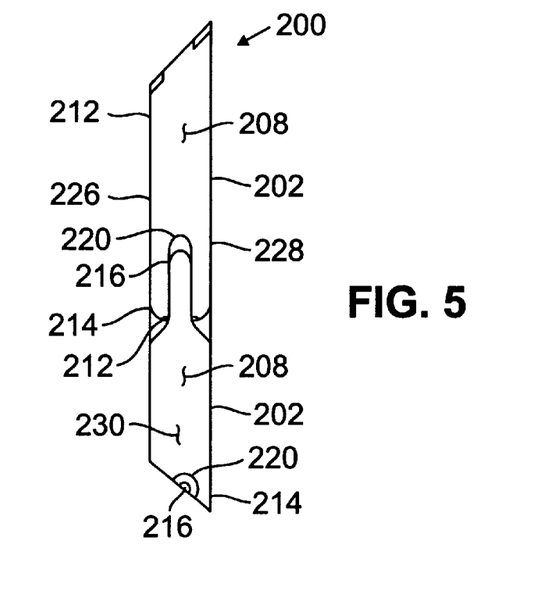
FIG. 5 shows a side elevational view of the band.
Figure 6:
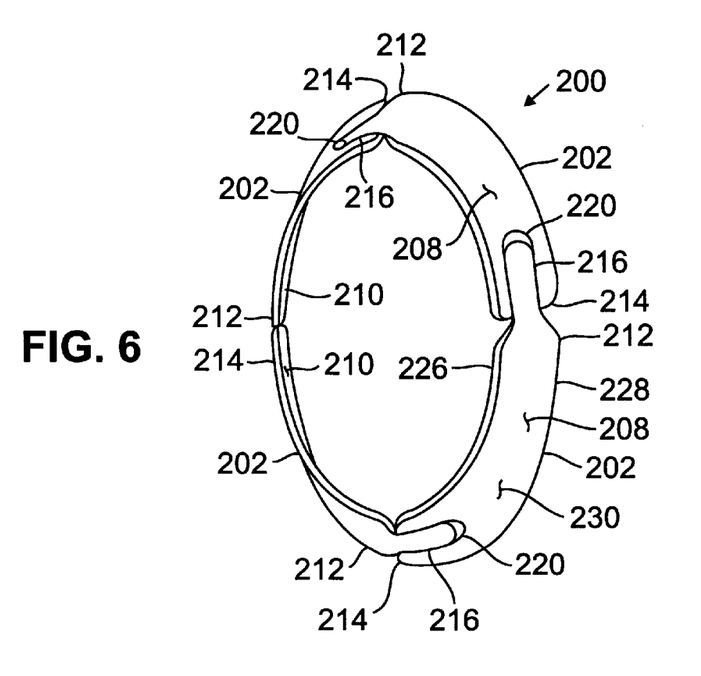
FIG. 6 shows an isometric view of the band.
Figure 7:
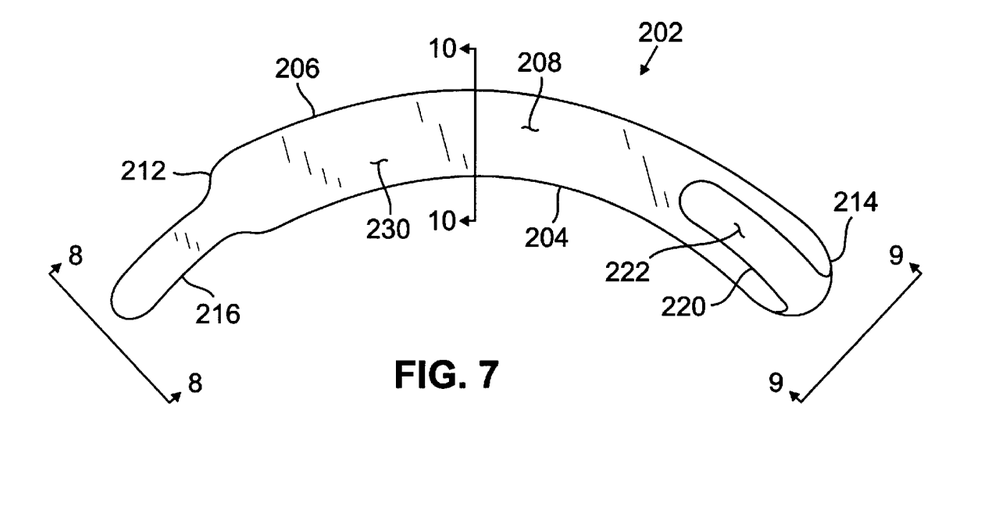
FIG. 7 shows a plan view of a segment of the band.
Figure 8:
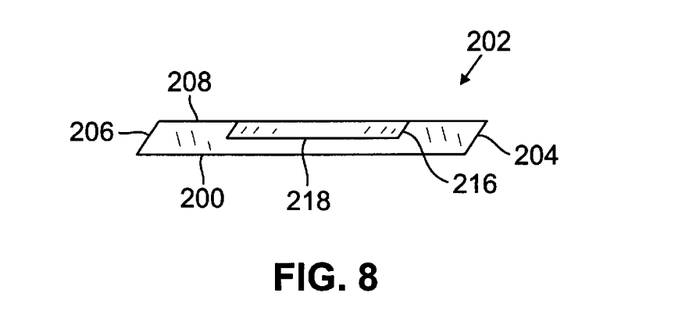
FIG. 8 shows an end view of a band segment as indicated by line 8—8 in FIG. 7.
Figure 9:
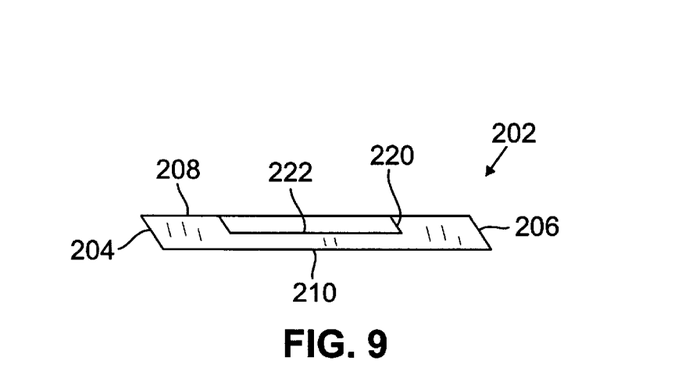
FIG. 9 shows an end view of a band segment as indicated by line 9—9 in FIG. 7.
Figure 10:
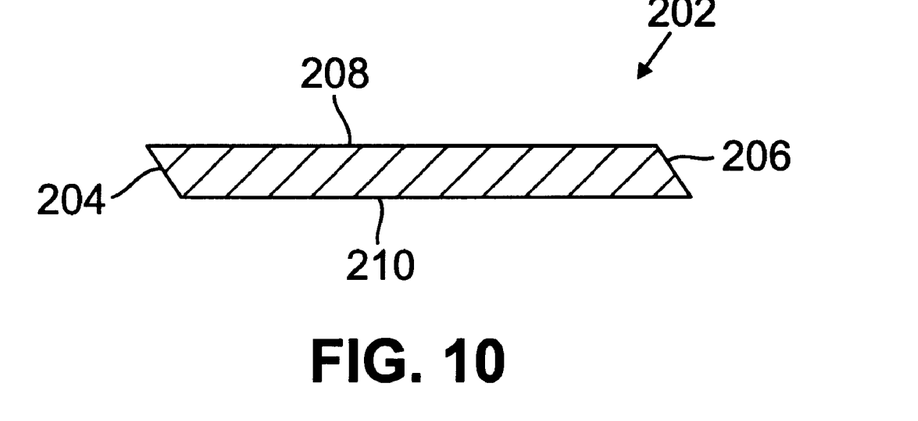
FIG. 10 shows a cross-sectional view of a band segment along line 10—10 in FIG. 7.
Figure 11:
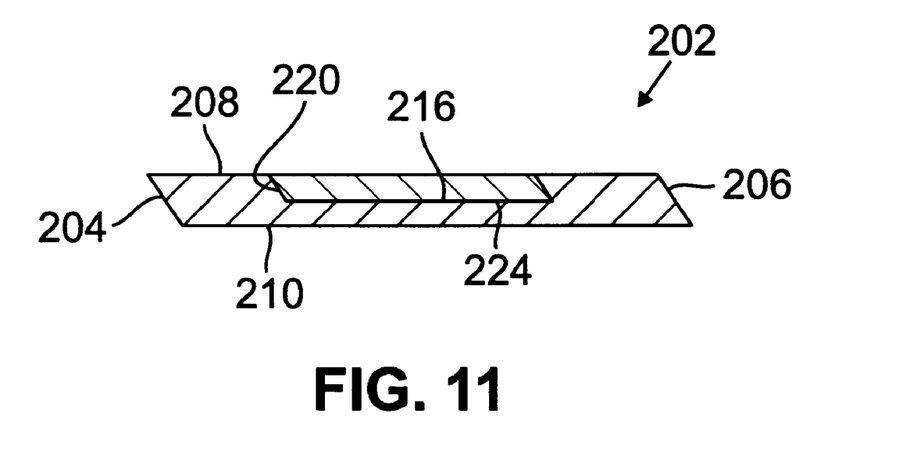
FIG. 11 shows a cross section of the fused tongue and groove portion of the segmented scleral band along lines 11—11 in FIG. 4.

Accordingly, each segment 202, as shown in FIGS. 9–10, has an anterior edge 204, a posterior edge 206, an outer surface 208, an inner surface 210, and two lateral ends 212 and 214. Although the illustrated embodiment of the segment shows a continuous web 230 of material connecting the anterior edge 204 and the posterior edge 206, the connecting structure 230 need not be such a continuous structure. Any structure, e.g., a web having apertures, or a lattice structure, is suitable, provided that the connecting structure has sufficient strength to keep the anterior edge 204 and the posterior edge 206 in their relative positions to provide the necessary rigidity to the assembled band 200. In the illustrated embodiment, one lateral end 212 of each segment 202 is provided with a tongue 216, and the other lateral end 214 is provided with a corresponding groove 218. After the segments are inserted through the scleral tunnels, the ends 212 and 214 are exposed as shown in FIG. 1. Each tongue 216 is then inserted into its corresponding groove 218, and the tongues 214 are then fastened in place within the grooves 218 to form the complete scleral band as shown in FIGS. 1, 4, and 5. Any means of fastening the segments 202 together is suitable. The segments may be bonded with an adhesive or welded or fused together, or a mechanical fastener, such as a screw or rivet can be used to fasten the ends of the segments 202 together. A preferred method of fastening the segments 202 together, when the segments are made from a preferred plastic material such as poly(methyl methacrylate) is to weld or fuse the lower surface 218 of the tongue 216 to the bottom 222 of the groove 220 by ultrasonic welding. The ultrasonic welding can be accomplished by conventional techniques. For example, the tongue 216 can first be positioned in the groove 220, then a support shoe is inserted under the end 214 of the segment 202 and an ultrasonic welding tool is applied to the tongue 216 for a time sufficient to form a fused welded area 224 (FIG. 11).

The segments 202 are typically dimensioned to fit snugly in the scleral tunnels. A typical segment will have a width of about 2 millimeters and a thickness of about 0.25 millimeters. The length of a typical segment, measured along the circumference from one end of the main body of the segment 202 to the other will be about 13 millimeters. The tongue will be about 3 millimeters in length. The skilled practitioner will understand that the dimensions will be adapted to the particular eye into which the scleral band is to be implanted. In particular, an assortment of lengths is typically made available to the surgeon so that segments can be selected that, when assembled on the globe of the eye, the completed scleral expansion band will be of the proper size to exert the desired outward traction on the sclera and ciliary body. If the segments 202 are made of a material that has some flexibility perpendicular to the surface thereof, e.g., a synthetic resin material, the segments can be made flat and curved to match the curvature of the globe of the eye when the band is implanted. If the band is made of a more rigid material it is preferable to form an appropriate curve before insertion. A typical segment of the preferred embodiment as illustrated will have a radius of curvature of the anterior rim of about 8.3 millimeters, and a corresponding radius of curvature of the posterior rim of about 10.3 millimeters. The radii of the rims can be accommodated to the particular dimensions of the eye into which the band is to be implanted.

Although the illustrated embodiment shows a tongue-and-groove design for joining the segments 202 that form the scleral band 200, the skilled practitioner will understand that other designs can be used as well. For example a simple butt joint effected by adhesive joining or welding could be used. Similarly, a lap joint or a tapered scarf joint can be used. Again one end of the segment 202 can be provided with a projection that fits into a recess or hole in end of the adjacent segment. The ends can be shaped to have complementary shapes that fit together much as a pieces of a jigsaw puzzle.

In practicing the method of the invention, the surgeon first locates the proper region or segment or zone of the sclera to be expanded by measuring a distance of preferably 2.0 millimeters posterior of the limbus. The scleral tunnels or pockets are then formed, preferably by the following procedure. At 2.5 millimeters clockwise and counterclockwise from each of the 45° meridians of the eye, and 2 millimeters posterior to the limbus, partial scleral thickness radial incisions, i.e., antero-posterior incisions, are made which are 2 millimeters long and 350 microns deep. Using a lamella blade the sclera is dissected until the partial thickness incisions are connected so that four scleral pockets or belt loops are made which have an anterior length of 5 millimeters, and a length extending generally axially of the eye of 2 millimeters. Thus, each pocket or belt loop is preferably centered over the 45° meridian of the eye. Each tunnel is directed generally circumferentially with respect to a circle defined generally by the intersection of the sclera with the plane of the equator of the crystalline lens, although the tunnels need not be exactly in that plane. A segment 202 of the scleral band 200 is then inserted in each pocket so that the ends 212 and 214 of the segments 202 meet in the spaces between the pockets, as shown in FIG. 1. The ends 212 and 214 of the segments 202 are then joined. In the illustrated embodiment the ends are joined by fitting the tongue 216 of one segment 202 into the groove 220 of the adjacent segment and fastening the tongue in the groove by ultrasonic welding or other joining technique as discussed above. The completed scleral band then produces symmetrical scleral expansion which will produce the desired result of increasing the effective working distance of the ciliary muscle.

The illustrated embodiment of the invention illustrates a preferred embodiment of the invention using use of four scleral tunnels and four scleral band segments. Fewer or more tunnels may be used at the surgeon's choice. It is not excluded that a single tunnel could be used with the segments of the band being joined through appropriate incisions.

The scleral band of the invention is made of a material that is sufficiently rigid to exert a force on the sclera sufficient to produce the radial expansion required by the method of the invention and that is physiologically acceptable for long-term implantation or contact with the ocular tissues. Such materials are well-known in the surgical art and include suitable metals, ceramics, and synthetic resins. Suitable metals include titanium, gold, platinum, stainless steel, tantalum, shape-memory alloys, and various surgically acceptable alloys, and the like. Suitable ceramics may include crystalline and vitreous materials such as porcelain, alumina, silica, silicon carbide, high-strength glasses and the like. Suitable synthetic materials include physiologically inert materials such as poly(methyl methacrylate), polyethylene, polypropylene, poly(tetrafluoroethylene), polycarbonate, silicone resins and the like.

The segment may also be made of composite materials incorporating a synthetic resin or other matrix reinforced with fibers of high strength material such as glass fibers, boron fibers or the like. Thus, the segment may be made of glass-fiber-reinforced epoxy resin, carbon fiber-reinforced epoxy resin, carbon fiber-reinforced carbon (carbon-carbon), or the like. A preferred material for the segment 202 is surgical grade poly(methyl methacrylate).

The segment of the scleral band of the invention may be manufactured by any conventional technique appropriate to the material used, such as machining, injection molding, heat molding, compression molding and the like.

The use of the scleral band of the invention to expand the sclera in the region of the ciliary body and increase the working distance of the ciliary muscle may also be of benefit in treatment of hyperopia in certain patients. Some youthful hyperopes can achieve relatively normal vision by compensating for their hyperopia through the natural accommodative ability of the eye. However, as this ability declines with age, they find that it becomes more difficult to attain normal vision by this process, and they begin to experience headaches and other symptoms, even at an age somewhat less than usual for the onset of presbyopia. Evidently, increasing the amplitude of accommodation by the method of this invention would be useful in restoring the ability of these patients to compensate for their hyperopia.

The method of this invention also has utility in the treatment of primary open-angle glaucoma, which shows a correlation with age in certain individuals. It has been found that, in general, intraocular pressure (IOP) exhibits a linear increase with increasing age. (Armaly, M. F., On the distribution of applanation pressure I. Statistical features and the effect of age, sex, and family history of glaucoma, Archives of Ophthalmology, Vol. 73, pp. 11–18 (1965)). Among the general population is found a group of individuals who develop abnormally high intraocular pressures as a result of primary open angle glaucoma, a disease which is one of the most prevalent causes of blindness in the world. According to the theory of this invention, the linear increase in IOP with age is a direct result of the decrease in distance between the lens equator and the ciliary muscle and the resulting linear decrease in the effective pull of the ciliary muscle. Since the ciliary muscle inserts into the trabecular meshwork, the decrease in pull will decrease the size of the trabeculum and/or the drainage pores and result in a linear increase of intraocular pressure with age. In this view, the patients who develop primary open angle glaucoma may have a congenital predilection to narrower pores, protein deposition in the pores, and/or a smaller trabecular meshwork, so that when the ability of the ciliary muscle to exert force declines, after the age of 40 or thereabouts, they tend to develop excessively elevated IOP.

The use of the scleral band of the invention to increase the effective working distance of the ciliary muscle, and thereby increase the force that it can exert when it contracts, restores the level of force which the ciliary muscle exerts on the trabecular meshwork to a value characteristic of a more youthful eye. In this way it is expected that the tendency of an eye that is disposed to develop primary open angle glaucoma as it ages would be overcome and the onset of this disease would be prevented or at least postponed.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

I claim:

1. A segmented scleral expansion band adapted for implantation within or fastening to a zone of the sclera of an eye lying outside of and adjacent to the ciliary body of the eye, said segmented scleral expansion band comprising a plurality of adjacent arcuate segments, each segment having a curved anterior edge and a curved posterior edge and structural spacing means extending between said anterior edge and said posterior edge and rigidly spacing said edges apart, each segment having lateral ends provided with means for fastening said ends of said adjacent segments together to form a band, said anterior edges and said posterior edges forming, when assembled into said band, an anterior rim and a posterior rim, respectively, of said band, and said segments being sized so that said anterior rim of said band will lie outside at least a portion of an anterior portion of said scleral zone and said posterior rim will lie outside at least a portion of a posterior portion of said scleral zone, at least one of said anterior rim, said posterior rim and said spacing means having a diameter greater than the exterior diameter of said scleral zone adjacent thereto.

2. The scleral expansion band of claim 1 wherein said fastening means comprises a tongue adapted to engage a recess on an adjacent segment.

3. The scleral expansion band of claim 2 wherein said recess is a groove.

4. The scleral expansion band of claim 1 wherein said band is made of a synthetic resin.

5. The scleral expansion band of claim 4 wherein said synthetic resin is selected from the group consisting of poly(methyl methacrylate), polyethylene, polypropylene, poly(tetrafluoroethylene) and silicone resins.

6. The scleral expansion band of claim 1 wherein said band is made of a reinforced composite material.

7. The scleral expansion band of claim 6 wherein said reinforced composite material is a glass-fiber reinforced synthetic resin.

8. The scleral expansion band of claim 6 wherein said reinforced composite material is a carbon-fiber reinforced material.

9. The scleral expansion band of claim 6 wherein said reinforced composite material is carbon-fiber reinforced carbon.

10. The scleral expansion band of claim 1 wherein said band is made of a physiologically acceptable metal.

11. The scleral expansion band of claim 10 wherein said band is made of metal selected from the group consisting of titanium, platinum, gold, tantalum, stainless steel, shape-memory alloys, and physiologically acceptable alloys.

12. The scleral expansion band of claim 1 wherein said band is made of a ceramic material.

13. The scleral expansion band of claim 12 wherein said ceramic is selected from the group consisting of porcelain, alumina, silica, silicon carbide, and high-strength glasses.

14. A segment of a scleral expansion band adapted to be assembled to form a scleral expansion band, said segment comprising a curved anterior edge and a curved posterior edge and structural spacing means extending between said anterior edge and said posterior edge and rigidly spacing said edges apart, said segment having lateral ends provided with means for fastening said ends to adjacent segments to form a scleral expansion band.

15. The segment of claim 14 wherein said fastening means comprises a tongue on one of said lateral ends and a groove on another of said lateral ends.

16. The segment of claim 14 wherein said anterior edge has a radius of curvature of about 8.0 to about 8.5 millimeters.

17. The segment of claim 16 wherein said anterior edge has a radius of curvature of about 8.3 millimeters.

18. The segment of claim 14 wherein said posterior edge has a radius of curvature of about 10.0 to about 10.5 millimeters.

19. The segment of claim 18 wherein said posterior edge has a radius of curvature of about 10.3 millimeters.

20. The segment of claim 14 wherein said segment is made of a synthetic resin.

21. The segment of claim 20 wherein said synthetic resin is selected from the group consisting of poly(methyl methacrylate), polyethylene, polypropylene, poly(tetrafluoroethylene) and silicone resins.

22. The segment of claim 14 wherein said segment is made of a reinforced composite material.

23. The segment of claim 22 wherein said reinforced composite material is a glass-fiber reinforced synthetic resin.

24. The segment of claim 22 wherein said reinforced composite material is a carbon-fiber reinforced material.

25. The segment of claim 24 wherein said reinforced composite material is carbon-fiber reinforced carbon.

26. The segment of claim 14 wherein said segment is made of a physiologically acceptable metal.

27. The segment of claim 26 wherein said segment is made of metal selected from the group consisting of titanium, platinum, gold, tantalum, stainless steel, shape-memory alloys, and physiologically acceptable alloys.

28. The segment of claim 14 wherein said segment is made of a ceramic material.

29. The segment of claim 28 wherein said ceramic is selected from the group consisting of porcelain, alumina, silica, silicon carbide, and high-strength glasses.

30. A method for restoring the amplitude of accommodation of an eye comprising forming at least one circumferentially oriented tunnel in the tissue of the sclera of an eye in a circumferential zone of the sclera lying outside the ciliary body of said eye, inserting in said tunnels segments of a scleral expansion band, and joining said segments to form a scleral expansion band, each of said segments of said scleral expansion band having a curved anterior edge and a curved posterior edge and structural spacing means extending between said anterior edge and said posterior edge and rigidly spacing said edges apart, each of said segments of said scleral expansion band having lateral ends provided with means for fastening said ends of said adjacent segments together to form a band, said anterior edges and said posterior edges forming, when assembled into said scleral expansion band, an anterior rim and a posterior rim, respectively, of said band, and said segments of said scleral expansion band being sized so that said anterior rim of said band will lie outside at least a portion of an anterior portion of said scleral zone and said posterior rim will lie outside at least a portion of a posterior portion of said scleral zone, at least one of said anterior rim, said posterior rim and said spacing means having a diameter greater than the exterior diameter of said scleral zone adjacent thereto.

* * * * *